United States Patent
Walker

(10) Patent No.: US 7,456,952 B2
(45) Date of Patent: *Nov. 25, 2008

(54) SYSTEM FOR REAL-TIME FLUORESCENT DETERMINATION OF TRACE ELEMENTS

(75) Inventor: Dwight Sherod Walker, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 132 days.

This patent is subject to a terminal disclaimer.

(21) Appl. No.: 11/531,469

(22) Filed: Sep. 13, 2006

(65) Prior Publication Data

US 2007/0091308 A1    Apr. 26, 2007

Related U.S. Application Data

(63) Continuation of application No. 10/363,294, filed as application No. PCT/US01/26892 on Aug. 29, 2001, now Pat. No. 7,277,168.

(60) Provisional application No. 60/228,673, filed on Aug. 29, 2000.

(51) Int. Cl.
 *G01J 3/30* (2006.01)
(52) U.S. Cl. .................................. 356/317; 250/458.1
(58) Field of Classification Search ................ 356/317, 356/318, 417; 250/458.1, 459.1
See application file for complete search history.

(56) References Cited

U.S. PATENT DOCUMENTS 4,577,110 A    3/1986 MacBride et al.
4,866,283 A    9/1989 Hill, Jr.
5,085,510 A    2/1992 Mitchell (Continued)

FOREIGN PATENT DOCUMENTS

DE    28 07 060    8/1979

(Continued)

OTHER PUBLICATIONS

Sung-Tag Oh, Tobru Sekiano, Koichi Niihara; Effect of Particle Size Distribution and Mixing Homogeneity on Microstructure and Strength of Alumina/Copper Composites, *NanoStructured Materials*, vol. 10, No. 2, pp. 327-332, 1998.

(Continued)

*Primary Examiner*—L. G Lauchman
(74) *Attorney, Agent, or Firm*—Robert J. Smith

(57) ABSTRACT

A system for use in in-situ analysis of pharmaceutical samples, said system comprising means for holding a plurality of said samples, wherein said samples are present in the form of a powder formulation; means for moving said plurality of samples along a sample path; means for generating a plurality of incident radiation pulses of different wavelength; means for illuminating at least a respective one of said samples with at least a respective one of said radiation pulses during said movement of said samples, said radiation pulse having a suitable range of radiation wavelengths capable of inducing a fluorescent response; means for detecting a first resultant fluorescence emitted from each of said samples; first control means in communication with said moving means and said incident radiation generating means for synchronizing said means for illuminating each of said samples with said moving means.

14 Claims, 7 Drawing Sheets

U.S. PATENT DOCUMENTS

| | | |
|---|---|---|
| 5,257,302 A | 10/1993 | Narukawa |
| 5,296,911 A | 3/1994 | Weyrauch et al. |
| 5,506,096 A | 4/1996 | Helmo |
| 5,663,997 A | 9/1997 | Willis et al. |
| 5,946,083 A | 8/1999 | Melendez et al. |
| 6,060,318 A | 5/2000 | Moeggenborg et al. |
| 6,310,687 B1 | 10/2001 | Stumbo et al. |
| 6,388,788 B1 | 5/2002 | Harris et al. |
| 6,567,163 B1 | 5/2003 | Sandstrom |
| 6,690,463 B2 | 2/2004 | Kask |
| 6,690,464 B1 | 2/2004 | Lewis et al. |
| 6,791,688 B2 | 9/2004 | Lai et al. |

FOREIGN PATENT DOCUMENTS

| | | |
|---|---|---|
| EP | 0122741 | 10/1894 |
| EP | 0767369 | 4/1997 |
| FR | 2 709 472 | 3/1995 |
| GB | 2 014 725 | 8/1979 |
| WO | 98/57153 | 12/1998 |
| WO | 00/03229 | 1/2000 |
| WO | 00/06078 | 2/2000 |

OTHER PUBLICATIONS

Tina S. Randall; Analysis of the Intrudction of New Technologies to Evaluate the Performanceof Pharmaceutical Unit Operations; Massachusetts Institute of Technology, 1998.

Communication pursuant to Article 96(2) EPC, date mailed Nov. 15, 2005, European Patent Office, EP Application No. 01966362.4.

Patent Abstracts of Japan, vol. 2000, No. 10, Nov. 17, 2000 & JP 2000 186915 A (Yuki Gijutsu Sogo:KK; Frontec Corp.; EISAI Co. LTD), Jul. 4, 2000 Abstract.

SYSTEM FOR REAL-TIME FLUORESCENT DETERMINATION OF TRACE ELEMENTS

CROSS-REFERENCE TO RELATED APPLICATIONS

The application is a continuation application of Ser. No. 10/363,294 filed Feb. 27, 2003 now U.S. Pat. No. 7,277,168, now allowed, which was filed pursuant to 35 U.S.C. § 371 as a United States National Phase Application of International Application No. PCT/US01/26892, filed Aug. 29, 2001, which claims priority from U.S. Provisional Application No. 60/228,673, filed Aug. 29, 2000.

FIELD OF THE PRESENT INVENTION

The present invention relates generally to spectroscopy systems. More particularly, the invention relates to a method and system for real-time fluorescent determination of trace elements.

BACKGROUND OF THE INVENTION

Beginning in the early 1970's, it was found that certain medicines could be administered in dry-powder form directly to the lungs by inhalation through the mouth or inspiration through the nose. This process allows the medicine to bypass the digestive system, and in some instances, allows smaller doses to be used to achieve the same desired results as orally ingested medicines.

Various metered dose powdered inhalers ("MDPI") or nebulizers that provide inhalable mists of medicines are known in the art. Illustrative is the devices disclosed in U.S. Pat. Nos. 3,507,277; 4,147,166 and 5,577,497.

Most of the prior art MDPI devices employ powdered medicine contained in a gelatin capsule. The capsules are typically pierced and a metered dose of the powdered medicine is slowing withdrawn by partial vacuum, forced inspiration of the user or by centrifugal force.

Several MDPI devices, such as that disclosed in U.S. Pat. No. 5,873,360 employs a foil blister strip. Referring to FIG. 1, the foil blister strip 10 includes a plurality of individual, sealed blisters (or pockets) 12 that encase the powdered medicine. The blisters 12 are similarly pierced during operation to release the metered dose of powdered medicine.

As will be appreciated by one having ordinary skill in the art, the provision of an accurate dosage of medicine in each capsule or blister is imperative. Indeed, the U.S. Government mandates 100% inspection of MDPI formulations to ensure that the formulations contain the proper amount of prescribed medicine or drug(s).

Various technologies have been employed to analyze MDPI formulations (i.e., pharmaceutical compositions), such as X-ray diffraction, high-pressure liquid chromatography (HPLC) and UV/visible analysis. There are, however, numerous drawbacks associated with the conventional technologies.

A major drawback of the noted technologies is that most require samples to be collected from remote, inaccessible, or hazardous environments, and/or require extensive sampling that is time consuming and prohibitively costly. A further drawback is that detection of minute amounts of trace elements, including the active ingredient or drug(s), is often difficult or not possible.

It is therefore an object of the present invention to provide a method and system for high-speed, real-time, on-line fluorescent assessment of active ingredients and trace elements.

It is another object of the present invention to provide a method and system for high-speed, real-time, on-line fluorescent detection of minute amounts of active ingredients and trace elements.

It is yet another object of the present invention to provide a method and system for high-speed, real-time, on-line fluorescent determination of the identity and concentration of active ingredients and trace elements.

SUMMARY OF THE INVENTION

In accordance with the above objects and those that will be mentioned and will become apparent below, the system for real-time fluorescent determination in accordance with this invention comprises means for moving a plurality of samples along a sample path; means for generating a plurality of incident radiation pulses of different wavelength; means for illuminating at least a respective one of the samples with at least a respective one of the radiation pulses during the movement of the samples, the radiation pulse having a suitable range of fluorescence radiation wavelengths; means for detecting the resultant fluorescence emitted from each of the samples; and first control means in communication with the moving means and the incident radiation generating means for synchronizing the means for illuminating each of the samples with the moving means.

The method for real-time fluorescent determination in accordance with this invention generally comprises moving a plurality of said samples having at least one element along a sample path; generating a plurality of incident radiation pulses of different wavelength; illuminating at least a respective one of the samples with at least a respective one of the radiation pulses during movement of the samples, the radiation pulse having a suitable range of fluorescence radiation wavelengths; detecting the resultant fluorescence emitted from each of said samples; and comparing the detected resultant fluorescence characteristics with stored fluorescence characteristics of pre-determined elements and/or active ingredients to identify the element or elements in the samples.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

The method and system of the present invention substantially reduces or eliminates the drawbacks and shortcomings associated with prior art methods and systems for in-situ detection and analysis of trace elements. As discussed in detail below, the system generally includes fluorescence detection means adapted to provide high-speed, accurate, in-situ determination of the presence, identity and concentration of trace elements and, in particular, active ingredients in pharmaceutical compositions. By the term "trace element", it is meant to mean and include an ingredient, component or element of a pharmaceutical composition or MDPI formulation having a relative concentration (i.e., % of total) of less than 0.5%, including, but not limited to, an active ingredient or element and medicament.

Figure 3:
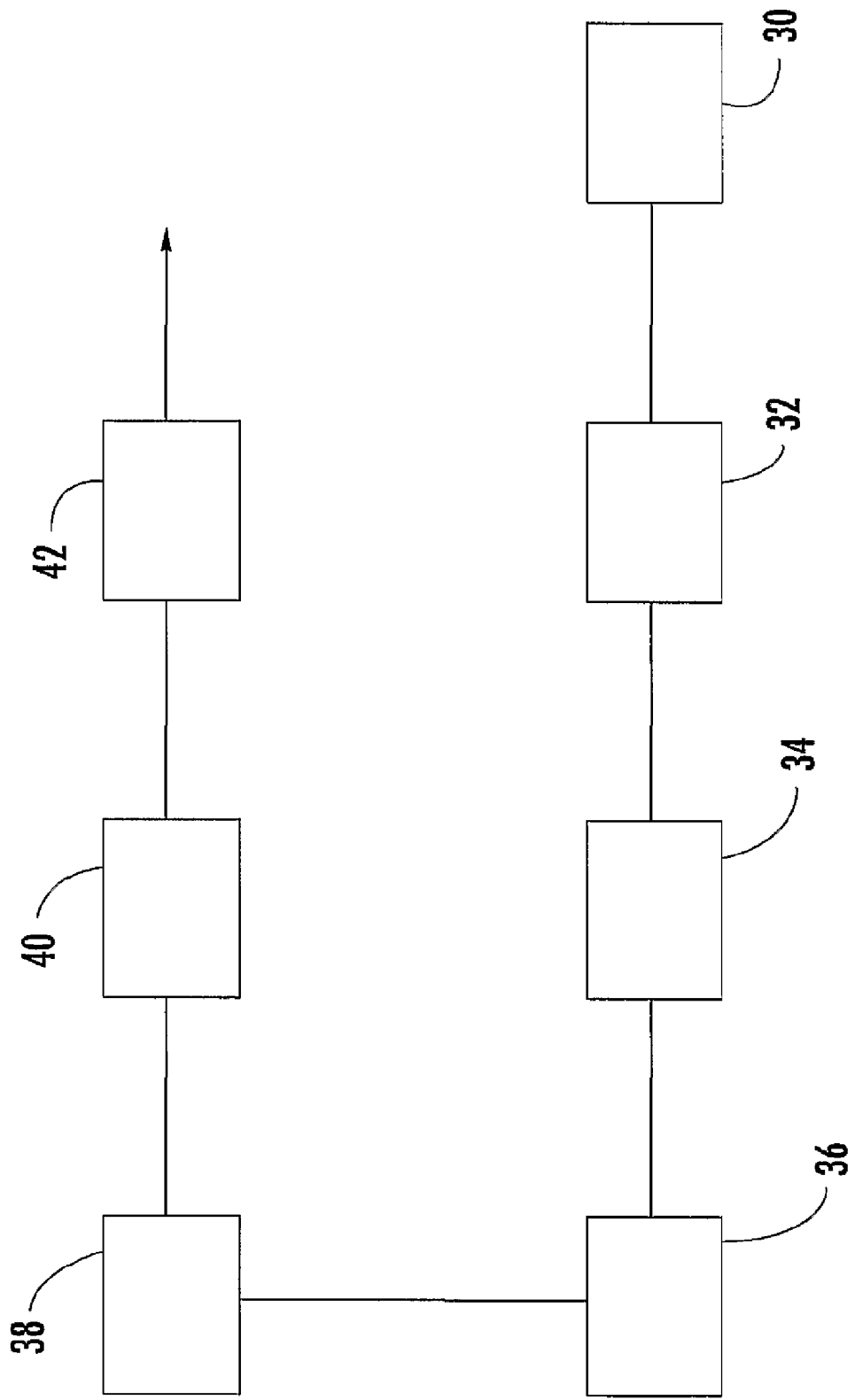
FIG. 3 is a flow chart of a conventional blister strip manufacturing process.
Figure 4:
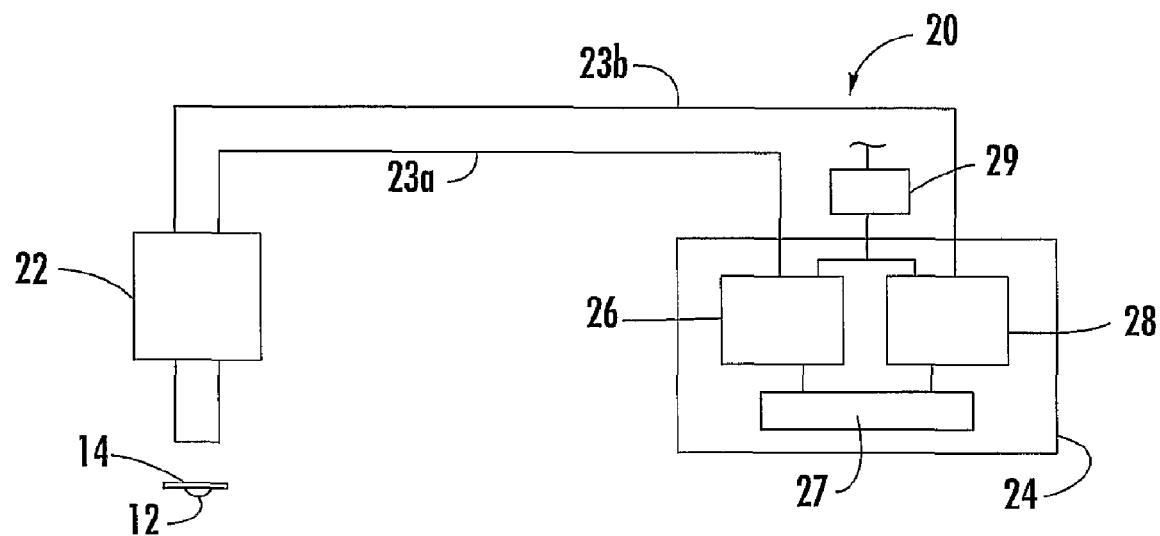
FIG. 4 is a schematic illustration of the fluorescence detection means according to the invention.

Referring first to FIG. 4, there is shown a schematic illustration of the fluorescence detection means (designated generally 20) of the invention. The fluorescence detection means 20 generally comprises at least one radiation transmission means 22 adapted to provide incident radiation to the sample 14 and detect the fluorescence (emission) radiation from the sample 14, and first control means 24. As illustrated in FIG. 3, the first control means 24 preferably includes a light source 26 for providing the desired wavelength of light or radiation to the radiation transmission means 22 via line 23a, an analyzer 28 for analyzing the emission radiation detected by the radiation transmission means 22, which is communicated to the analyzer 28 via line 23b, and storage means for storing fluorescence characteristics of known elements (or ingredients) for subsequent comparison with detected emission (fluorescence) radiation from the sample(s) 14.

As discussed in detail below, the fluorescence detection means 20 further includes second control means 29 preferably in communication with the light source 26, analyzer 28 and conveyor system 50 for synchronizing the movement of the samples 14 on the conveyor system 50 with the incident radiation transmission and detection of the resultant emission radiation (See FIG. 7).

As is well known in the art, for fluorescence measurements, it is necessary to separate the emission (or emitted) radiation from the incident radiation. This is typically achieved by measuring the emission radiation at right angles to the incident radiation.

Figure 5:
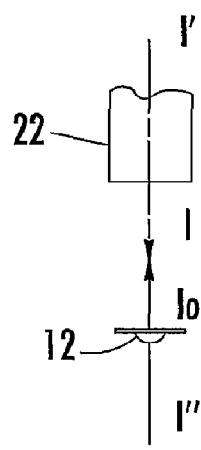
FIG. 5 is a partial plan view of the radiation transmission means, illustrating the travel of the incident and emitted radiation according to the invention.

However, as illustrated in FIG. 5, in a preferred embodiment of the present invention, the emission radiation, $I_o$, is measured (or detected) along a line I" that is substantially coincident to the line I' defined by the travel of the incident radiation I. According to the invention, the wavelength of the emission radiation $I_o$ is "red shifted" to an upper frequency.

It is further well established that the relationship between the trace element concentration and the fluorescence intensity (i.e., emission radiation) can be derived from Beer's Law, i.e., $$F = \Phi P_O(1 - 10^{-\alpha bc})$$ EQ-1 where:
  F=Fluorescence Intensity
  $P_O$=Power of incident radiation
  $\alpha$=Molar Absorbtivity
  b=Path length
  c=Sample concentration (moles/liter)
  $\Phi$=Quantum yield—a proportionality constant and a measure of the fraction of absorbed photons that are converted into fluorescent photons.

It is thus evident that the quantum yield, $\Phi$, is generally less than or equal to unity. It is further evident from Eq. 1 that if the product $\alpha bc$ is large, the term $10^{-\alpha bc}$ becomes negligible compared to 1, and F becomes constant:

$$F = \Phi P_0$$ Eq. 2

Conversely, if the product $\alpha bc$ is small ($\leq 0.01$), it can be shown (i.e., Taylor expansion series) that the following provides a good approximation of the fluorescence intensity:

$$F = 2.303 \Phi P_O \alpha bc$$ Eq. 3

Accordingly, for low concentrations of trace elements, the fluorescence intensity is directly proportional to the concentration. The fluorescence intensity is also directly proportional to the incident radiation.

Since the noted relationships hold for concentrations up to a few parts for million, Eq.3 is preferably employed in the method of the invention to determine the concentration of the trace element(s) detected by the fluorescence detection means 22.

Referring now to FIG. 3, there is shown a flow chart of a conventional blister strip process, illustrating the primary steps involved in the manufacture of a foil blister strip. According to the process, the base foil is fed from a coil 30 to the forming operation 32.

Figure 1:
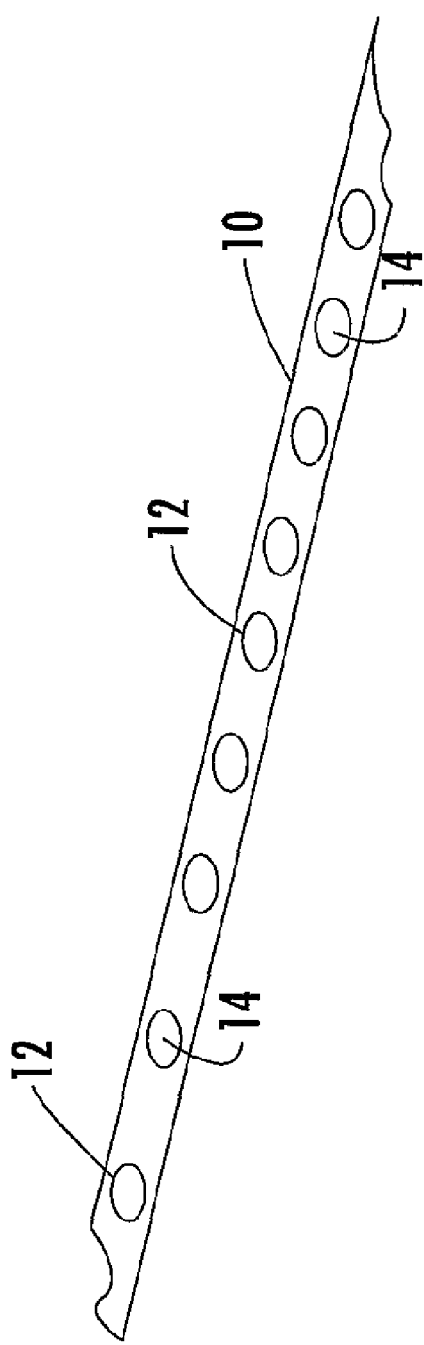
FIG. 1 is a perspective view of a prior art foil blister strip.
Figure 2:
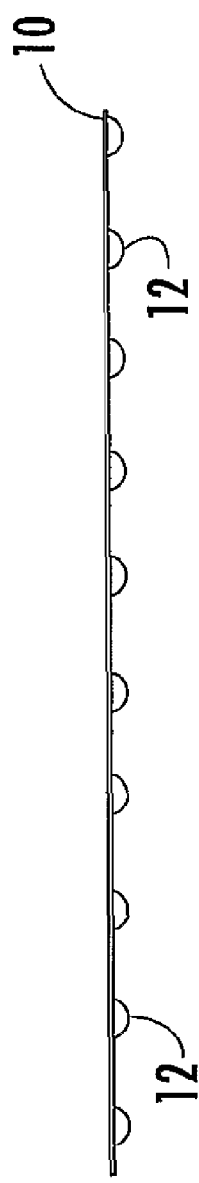
FIG. 2 is a side plan view of the foil blister strip shown in FIG. 1.

After the blisters 12 are formed on the strip 10 (see FIGS. 1 and 2), the strip 10 is inspected for defects 34 and, in particular, pin holes. Each blister 12 on the strip 10 is then filled 38 with a desired MDPI formulation or pharmaceutical composition.

After filling, the strip 10 is subjected to a second inspection 40. The second inspection typically comprises a complete chemical analysis of the pharmaceutical composition to determine the presence of all ingredients or elements and the respective concentrations thereof.

As discussed above, the noted inspection 40 typically involves the removal of a sample, transfer of the sample to an off-line location or facility, and HPLC or UV/vis analysis. The operation is thus time consuming and expensive.

After the inspection 40, the appropriate code is applied 42 to the strip 12. The strip is then transferred to a storage roll.

Figure 6:
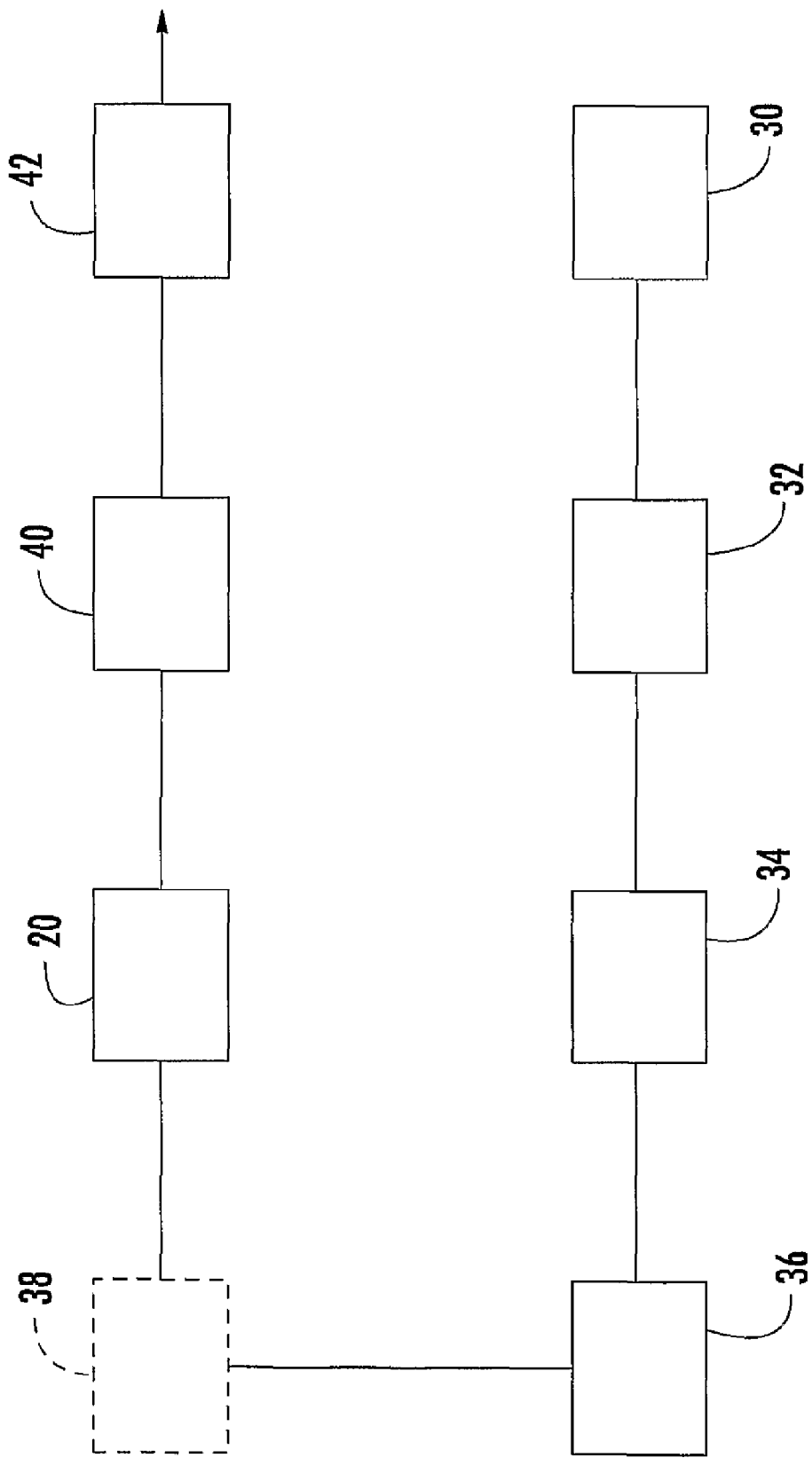
FIG. 6 is a further flow chart of a conventional foil blister strip manufacturing process, illustrating the incorporation of the fluorescence detection means according to the invention.

Referring now to FIG. 6, there is shown a further flow chart of the above discussed blister strip process, illustrating the incorporation of the fluorescence detection means 20 of the invention. As illustrated in FIG. 6, the fluorescence detection means 20 is preferably disposed between the filling 38 and sealing 40 operations.

As will be appreciated by one having ordinary skill in the art, the fluorescence detection means 20 of the invention is readily adaptable to most processes. Further, due to the inherent accuracy and tight specifications (that are possible by virtue of the detection means 20), the conventional inspection (i.e., analysis) operation/step 38 can be eliminated. However, as illustrated in FIG. 6, the fluorescence detection means 20 can also be employed in conjunction with the conventional inspection operation 3 8 (shown in phantom).

Figures 7, 8:
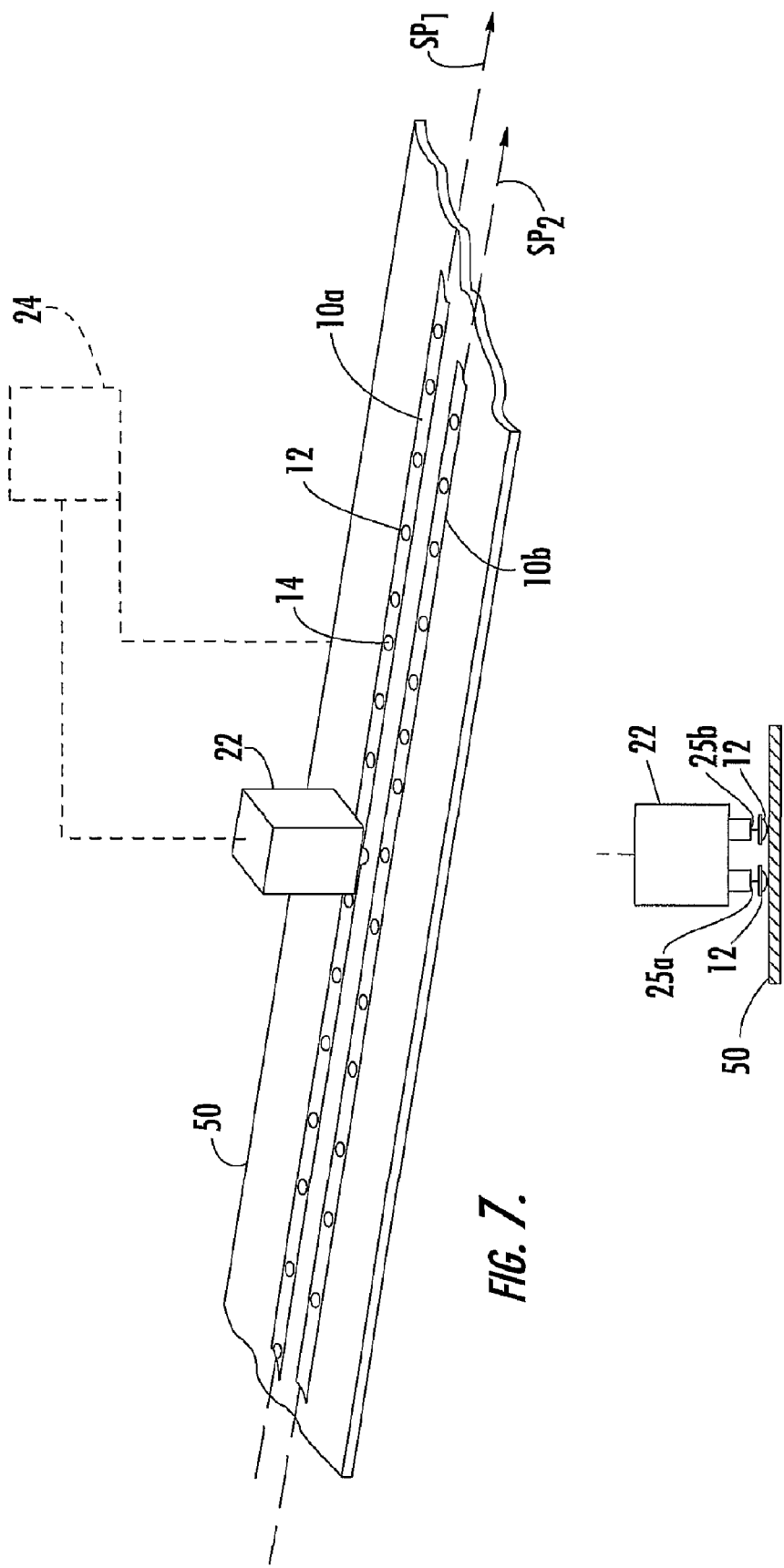
FIG. 7 is a perspective view of a conventional conveyor and the fluorescence detection means according to the invention.
FIG. 8 is a partial section, front plan view of the conveyor and fluorescence detection means shown in FIG. 7.

Referring to FIGS. 7 and 8, the fluorescence detection means 20 of the invention will now be described in detail. Referring first to FIG. 7, there is shown a conventional conveyor system 50 adapted to facilitate the transfer of two blister strips 10a, 10b to the above noted operations 30, 32, 36, 20, 40, 42. As illustrated in FIG. 7, the radiation transmission means 22 is disposed proximate the conveyor system 50 and, hence, blister strips 10a, 10b positioned thereon.

In a preferred embodiment of the invention, the radiation transmission means 22 comprises a J.Y. Horiba fluorometer that is adapted to provide two lines of incident radiation (or incident radiation pulses) 25a, 25b. According to the invention, the first line of incident radiation 25a is directed toward and substantially perpendicular to the first blister strip 10a and, hence, sample path (designated generally $SP_1$) and the second line of incident radiation 25b is directed toward and substantially perpendicular to the second sample path (designated generally $SP_2$). In additional envisioned embodiments of the invention, not shown, the radiation transmission means 22 is adapted to provide one line of incident radiation (e.g., 25a) to facilitate a single (rather than dual) blister strip process.

In a preferred embodiment of the invention, the first control means 24 generates and provides a plurality of incident radiation pulses of different wavelengths, preferably in the range of 200 to 800 nm. According to the invention, at least a respective one of the samples 14 is illuminated with at least a respective one of the incident radiation pulses as it traverses a respective sample path $SP_1$, $SP_2$. In a preferred embodiment, each sample 14 passing under the radiation transmission means 22 is illuminated with incident radiation over a pre-determined, suitable range of wavelengths capable of inducing a fluorescence response in at least one target element (or ingredient).

Applicants have found that the noted incident radiation wavelength range will induce a definitive fluorescence response in trace elements and, in particular, active ingredients, having a relative concentration in the range of 0.3 to 0.5%.

As discussed above, the emission (fluorescence) radiation is detected by the radiation transmission means 22 and at least a first signal indicative of the sample fluorescence characteristics is communicated to the analyzer 28. According to the invention, the emission radiation, is then compared to the stored fluorescence characteristics of known elements to identify the element or elements (or trace element(s)) in the samples 14. The concentration of the element(s) can also be determined through the formulations referenced above (e.g., Eq. 3).

As also indicated above, the fluorescence detection means 20 is further adapted to be in synchrony with the conveyor system 50. In a preferred embodiment of the invention, the fluorescence detection means 20 includes second control means 29 that is in communication with the first control means 24 and conveyor system 50. The second control means 29 is designed and adapted to synchronize the movement of the samples 14 on the conveyor system 50 with the illumination of each sample 14 as it traverses a respective sample path $SP_1$, $SP_2$. Thus, 100% inspection of each sample 14 contained in the blisters 12 is ensured.

Further, the noted synchronized sample fluorescence detection and analysis is preferably accomplished at a rate (or speed) of approximately 1 sample/sec. Thus, the method and system of the invention provides high speed, accurate, on-line analysis of MDPI formulations and other pharmaceutical compositions that is unparalleled in the art.

The present invention will now be illustrated with reference to the following examples. The examples are provided for illustrative purposes only, and are not intended to limit the scope of the invention.

EXAMPLE 1

Figure 9:
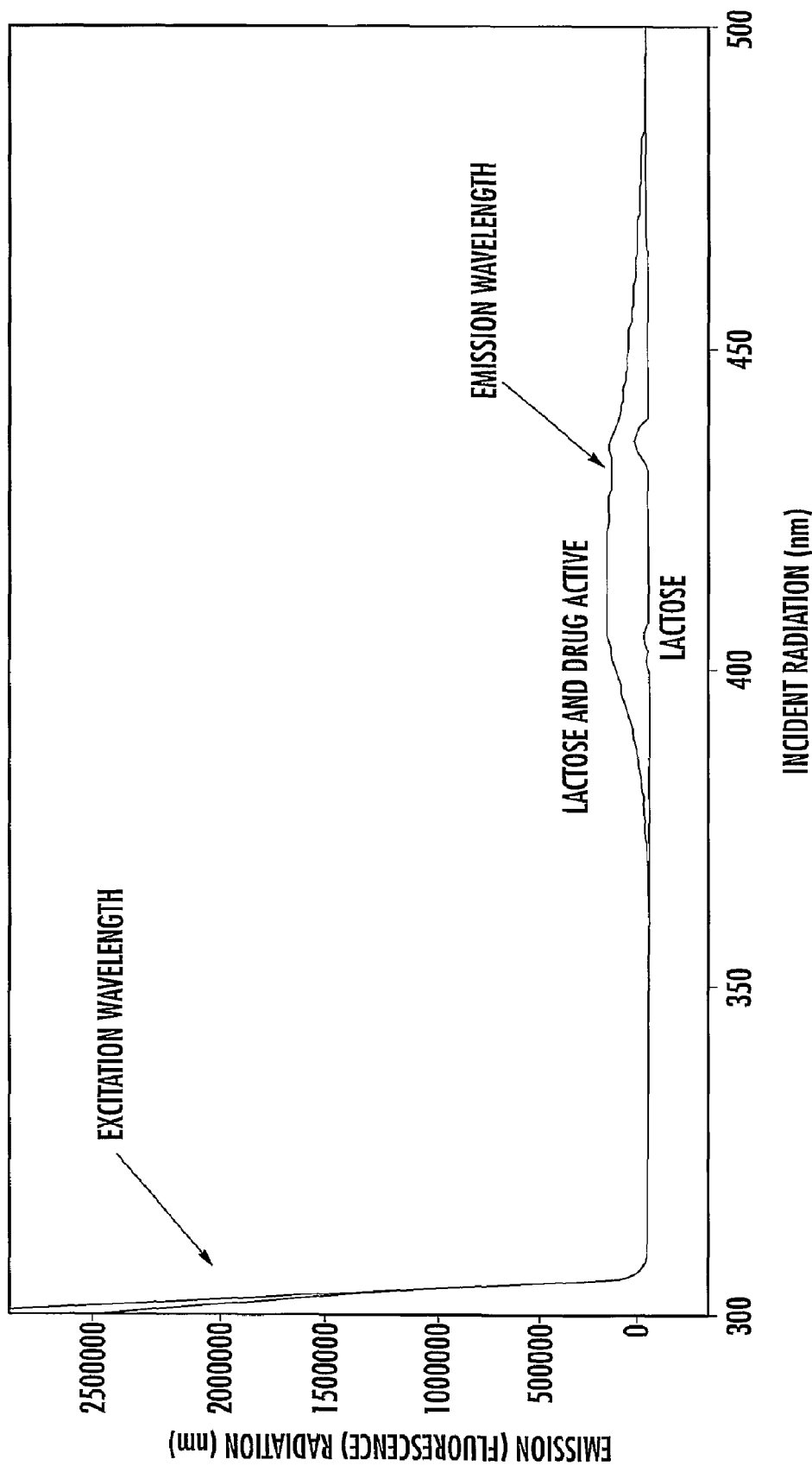
FIGS. 9 and 10 are graphs of incident radiation versus emission radiation for prepared compounds, illustrating the detection of low concentration active trace elements according to the invention.

A MDPI formulation comprising >99.5% lactose and <0.5% active ingredient was prepared. Referring to FIG. 9, the MDPI formulation and a reference lactose sample were then subjected to a pre-determined, suitable range of incident radiation to induce a fluorescent response. As will be appreciated by one having ordinary skill in the art, the incident radiation is determined by and, hence, dependent upon the target ingredient or element of the MDPI formulation.

As illustrated in FIG. 9, a definitive fluorescent response, reflecting the detection of the active ingredient was provided with an incident radiation level in the range of approx. 350 nm to 500 nm. The noted fluorescence spectra further indicates that an active ingredient or trace element having a relative concentration of less than 0.5% can readily be detected by virtue of the fluorescence detection means of the invention.

As will be appreciated by one having ordinary skill in the art, the noted fluorescence spectra can be compared to stored calibration (or reference) spectra by conventional means to identify the detected active ingredient (or trace element). Further, as discussed above, the concentration of the detected active ingredient can also be determined through known formulations (See Eq. 3).

Applicants have further found that subjecting the MDPI formulation to subsequent incident radiation in the same range provides little, if any, variation in the detected emission radiation. Indeed, the fluorescence spectra obtained were virtually identical.

Accordingly, by virtue of the fluorescence detection means of the invention, a tolerance level of ±0.5 nm (i.e., calibration emission radiation ±0.5 nm) can be employed. As will be appreciated by one having ordinary skill in the art, the noted tight "QC" specification is unparalleled in the art.

EXAMPLE 2

Figure 10:
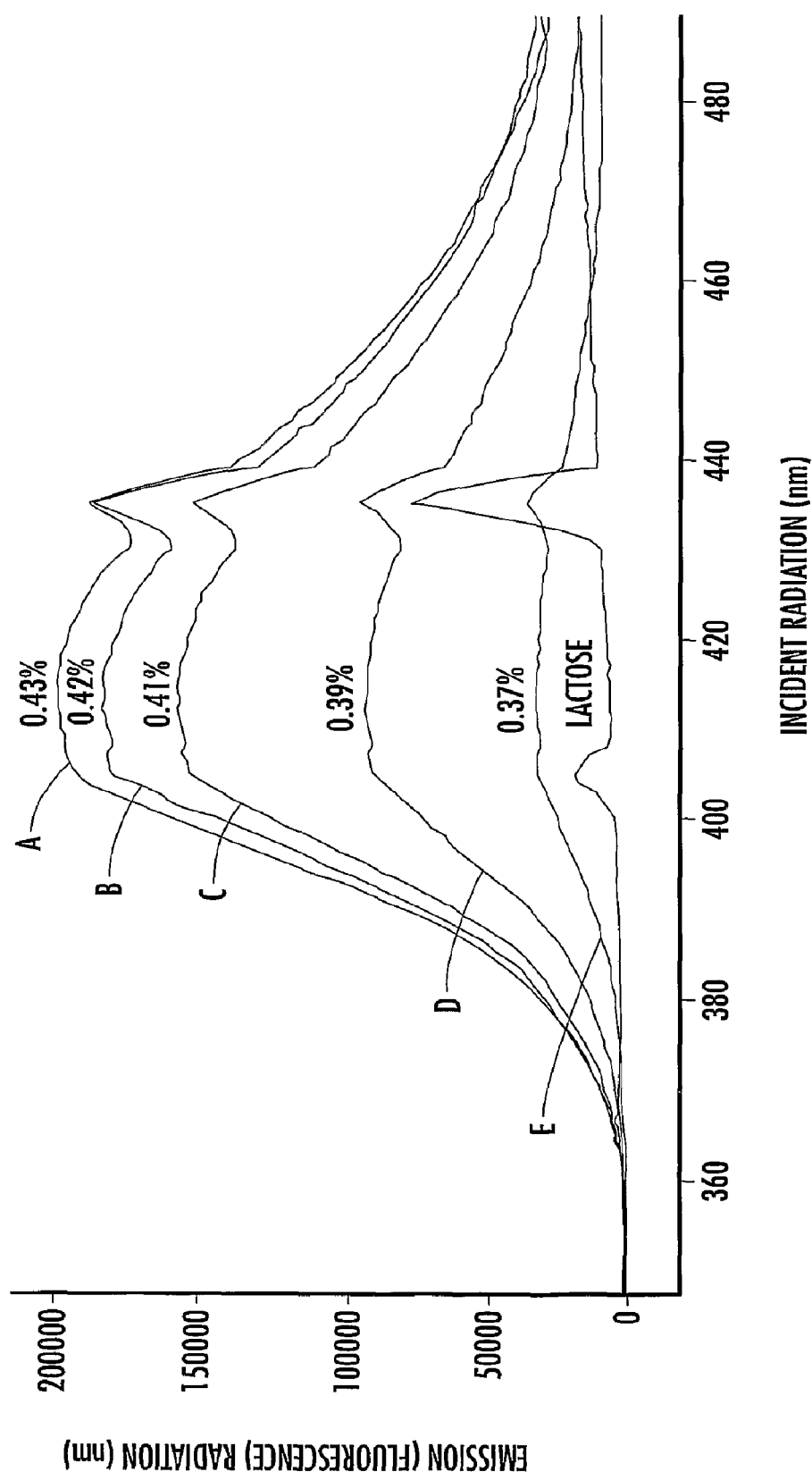

Referring now to FIG. 10, there are shown the fluorescence spectra of similar MDPI formulations having ~0.43% active ingredient (Curve A); ~0.42% active ingredient (Curve B); ~0.41% active ingredient (Curve C); ~0.39% active ingredient (Curve D); and ~0.37% active ingredient (Curve E). The noted fluorescence spectra were similarly induced with an incident radiation level in the range of approximately 350 to 500 nm.

The fluorescence spectra (i.e., Curves A-E) further demonstrate that a sharp, definitive fluorescent response can be achieved in active ingredients having a relative concentration in the range of approx. 0.37% to 0.43% by virtue of the fluorescence detection means of the invention.

As will be appreciated by one having ordinary skill in the art, a narrower band or range of incident radiation (e.g., 375-475 nm) could also be employed to identify and determine the relative concentration of an active ingredient. Further, an even narrower range of incident radiation wavelengths (e.g., 400-425 nm) or incident radiation with a single wavelength within the noted range (e.g., 410 nm) could be employed to determine active ingredient "presence".

SUMMARY

From the foregoing description, one of ordinary skill in the art can easily ascertain that the present invention provides a method and system for high speed, real-time, 100% fluorescent inspection of MDPI formulations and other pharmaceutical compositions. The method and system of the present invention further provides an accurate determination of (i) the presence (i.e., qualitative assessment), and (ii) identity and concentration (i.e., quantitative assessment) of active ingredients and/or other trace elements having a relative concentration in the range of approximately 0.3 to 0.5% p Without departing from the spirit and scope of this invention, one of ordinary skill can make various changes and modifications to the invention to adapt it to various usage and conditions. As such, these changes and modifications are properly, equitably, and intended to be, within the full range of equivalence of the following claims.

What is claimed:

1. A system for use in in-situ analysis of pharmaceutical samples, said system comprising:
    means for holding a plurality of said samples, wherein said samples are present in the form of a powder formulation;
    means for moving said plurality of samples along a sample path;
    means for generating a plurality of incident radiation pulses of different wavelength;
    means for illuminating at least a respective one of said samples with at least a respective one of said radiation pulses during said movement of said samples, said radiation pulse having a suitable range of radiation wavelengths capable of inducing a fluorescent response;
    means for detecting a first resultant fluorescence emitted from each of said samples;
    first control means in communication with said moving means and said incident radiation generating means for synchronizing said means for illuminating each of said samples with said moving means.

2. The system of claim 1, including second control means for analyzing second resultant fluorescence emitted from each of said samples.

3. The system of claim 1, wherein said plurality of incident radiation pulses of different wavelength is in the range of 200 to 800 nm.

4. A system for use in determining the presence and concentration of trace elements in a sample, said system comprising:
    means for holding a plurality of said samples, wherein said samples are present in the form of a powder formulation, each of said plurality of samples including at least one of said trace elements;
    means for moving said plurality of samples along a sample path;
    means for generating a plurality of incident radiation pulses of different wavelengths;
    means for illuminating at least a respective one of said samples with at least a respective one of said radiation pulses during said movement of said samples, said radiation pulse having a suitable range of radiation wavelengths capable of inducing a fluorescent response;
    means for detecting a resultant fluorescence response emitted from said trace element; and first control means in communication with said moving means and said incident radiation generating means for synchronizing said means for illuminating each of said samples with said moving means.

5. The system of claim 4, including second control means for storing fluorescence characteristics of pre-determined elements and means for comparing said detected resultant fluorescence emitted from said trace element to identify said trace element in said plurality of samples, said second control means including means for determining the relative concentration of said trace element in each of said samples.

6. The system of claim 4, wherein said trace element has a relative concentration in the range 0.3 to 0.5%.

7. The system of claim 4, wherein said plurality of incident radiation pulses of different wavelength range from 200 to 800 nm.

8. A system for use in in-situ analysis of pharmaceutical composition samples, said system comprising:
    means for holding a plurality of samples, wherein said samples are present in the form of a powder formulation, said samples including at least one trace element;
    means for substantially simultaneously moving said plurality of samples along a sample path, illuminating at least a respective one of said samples with incident radiation having one or more suitable wavelengths during said movement of said plurality of samples, and detecting a result in emission radiation from said samples; and control means in communication with said illuminating and detecting means for providing a range of radiation and analyzing said result in emission radiation and fluorescence emitted from said samples.

9. The system of claim 8, wherein said incident radiation is directed along a first radiation path that intersects said sample path and is substantially perpendicular thereto.

10. The system of claim 8, wherein said emitted radiation is substantially detected along a second radiation path, said second radiation path being substantially coincident with said first radiation path.

11. The system of claim 8, wherein said samples are moved by said moving means at a minimum rate of one sample per second.

12. The system of claim 8, wherein said incident radiation has a plurality of different wavelengths in the range of 200 to 800 nm.

13. The system of claim 8, wherein said trace element has a relative concentration in the range of 0.3 to 0.5%.

14. A system for use in in-situ analysis of pharmaceutical samples, said system comprising:
    a holder for holding a plurality of said samples, wherein said samples are present in the form of a powder formulation;
    a conveyor system for moving said plurality of samples along a sample path;
    at least one radiation transmitter for generating a plurality of incident radiation pulses of different wavelength;
    an illuminator for illuminating at least a respective one of said samples with at least a respective one of said radiation pulses during said movement of said samples, and radiation pulse having a suitable range of radiation wavelengths capable of inducing a fluorescent response;
    a radiation detector for detecting a first resultant fluorescence emitted from each of said samples;
    a first controller in communication with said conveyor system and said radiation transmitter for synchronizing said illuminator with said conveyor system.

* * * * *